(12) United States Patent
Smith

(10) Patent No.: US 8,518,056 B2
(45) Date of Patent: Aug. 27, 2013

(54) DEVICE FOR APPLYING SUCCESSIVE RESILIENT LIGATING BANDS TO TISSUE

(76) Inventor: Alan Smith, Bromley (GB)

( * ) Notice: Subject to any disclaimer, the term of this patent is extended or adjusted under 35 U.S.C. 154(b) by 83 days.

(21) Appl. No.: 13/239,531

(22) Filed: Sep. 22, 2011

(65) Prior Publication Data

US 2012/0078272 A1 Mar. 29, 2012

(30) Foreign Application Priority Data

Sep. 24, 2010 (EP) ..................................... 10179178

(51) Int. Cl.
*A61B 17/10* (2006.01)

(52) U.S. Cl.
USPC .......................................... 606/140; 606/139

(58) Field of Classification Search
USPC .................. 606/135, 139, 140, 141, 142, 144, 606/148, 151, 165; 206/63.3, 438; 600/104
See application file for complete search history.

(56) References Cited

U.S. PATENT DOCUMENTS

| | | | |
|---|---|---|---|
| 4,735,194 A | 4/1988 | Stiegmann | |
| 5,320,630 A | 6/1994 | Ahmed | |
| 5,462,559 A | 10/1995 | Ahmed | |
| 5,624,453 A | 4/1997 | Ahmed | |
| 6,136,009 A | 10/2000 | Mears | |
| 6,436,108 B1 * | 8/2002 | Mears | 606/140 |
| 7,488,333 B2 | 2/2009 | Ghareeb | |
| 2002/0072757 A1 | 6/2002 | Ahmed et al. | |
| 2005/0143757 A1 * | 6/2005 | Ghareeb | 606/139 |
| 2006/0259042 A1 | 11/2006 | Ali Hassanien | |
| 2008/0015613 A1 | 1/2008 | Saeed et al. | |

FOREIGN PATENT DOCUMENTS

| | | |
|---|---|---|
| EP | 0679368 A1 | 11/1995 |
| EP | 1077648 A1 | 2/2001 |
| EP | 1511431 A1 | 3/2005 |
| GB | 2388783 A | 11/2003 |
| GB | 2426459 A | 11/2006 |
| WO | 99/56635 A1 | 11/1999 |
| WO | 03/099141 A1 | 12/2003 |
| WO | 2005/112797 A1 | 12/2005 |

OTHER PUBLICATIONS

European Search Report dated Mar. 2, 2011 in corresponding European Patent Application No. EP 10179178.

* cited by examiner

*Primary Examiner* — Corrine M McDermott
*Assistant Examiner* — Robert A Lynch
(74) *Attorney, Agent, or Firm* — Neilds, Lemack & Frame, LLC

(57) ABSTRACT

A device for applying successive resilient ligating bands to tissue is described. A sleeve has an opening at a front end thereof, and axially extending arms having axially extending spaces therebetween. Band-support surfaces located on the arms extend from the front end for accommodating a plurality of ligating bands. A first tube around which the sleeve is located, is reciprocal relative to the sleeve and has axially extending fingers provided with forward-facing pushing surfaces. Means are provided for drawing tissue to be ligated into the opening. In use, the pushing surfaces push the bands forwardly so that they ride along the band-support surfaces of the sleeve to each lie nearer the front end, a foremost band being pushed off the front end of the sleeve onto the tissue.

23 Claims, 13 Drawing Sheets

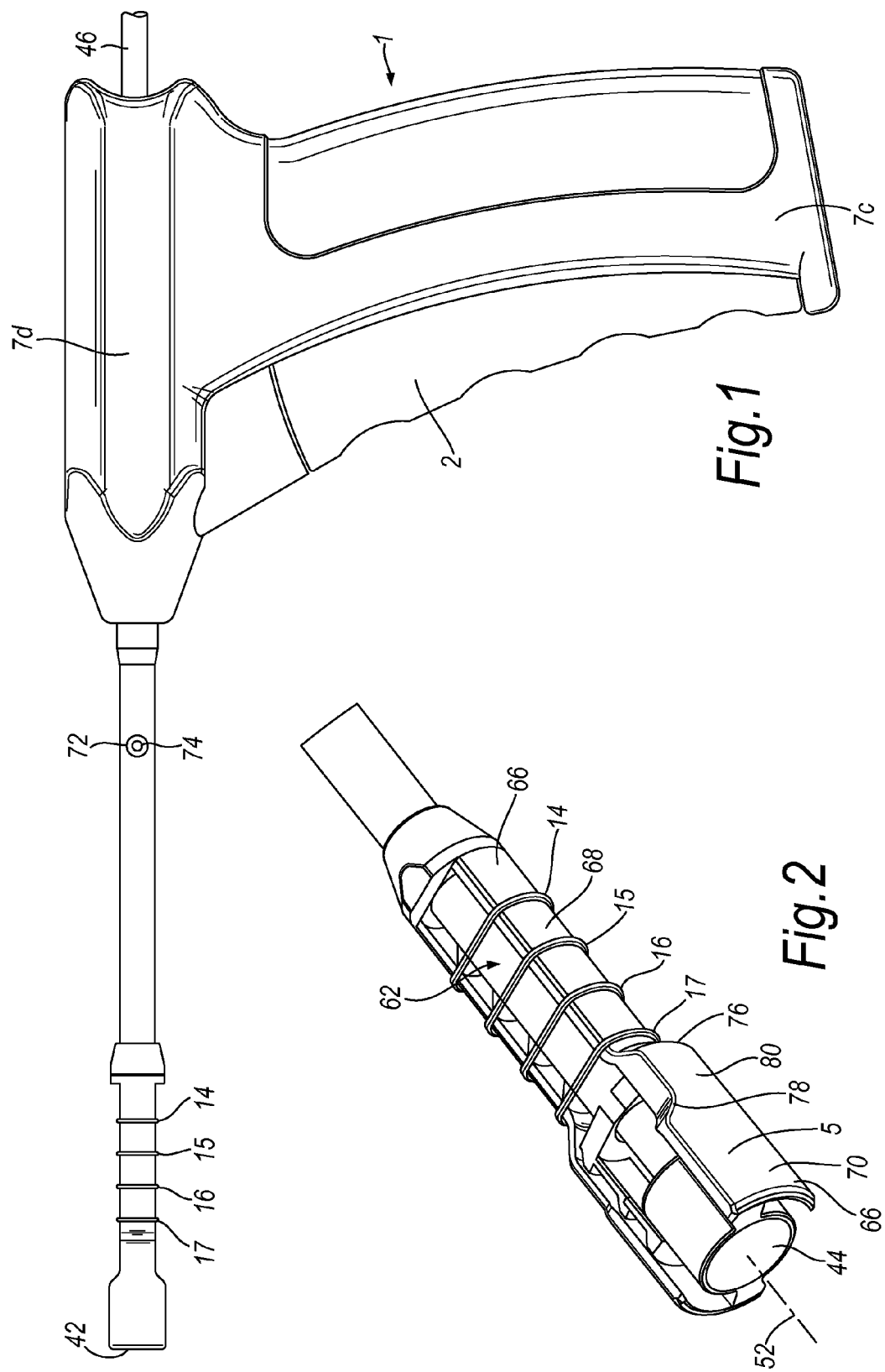

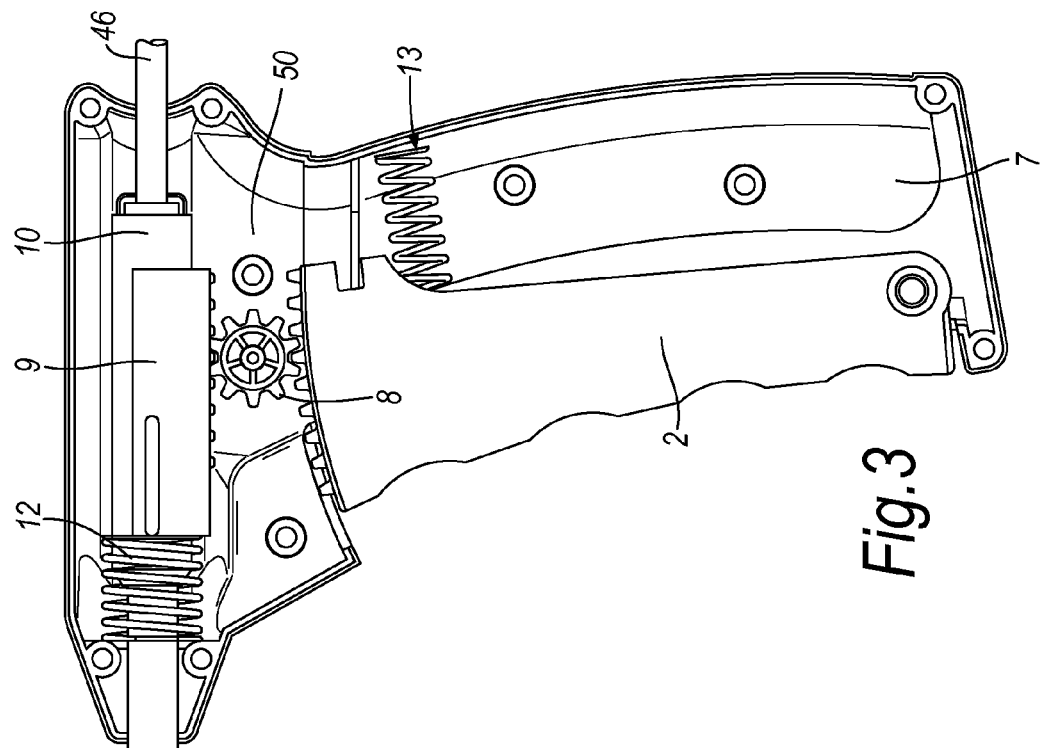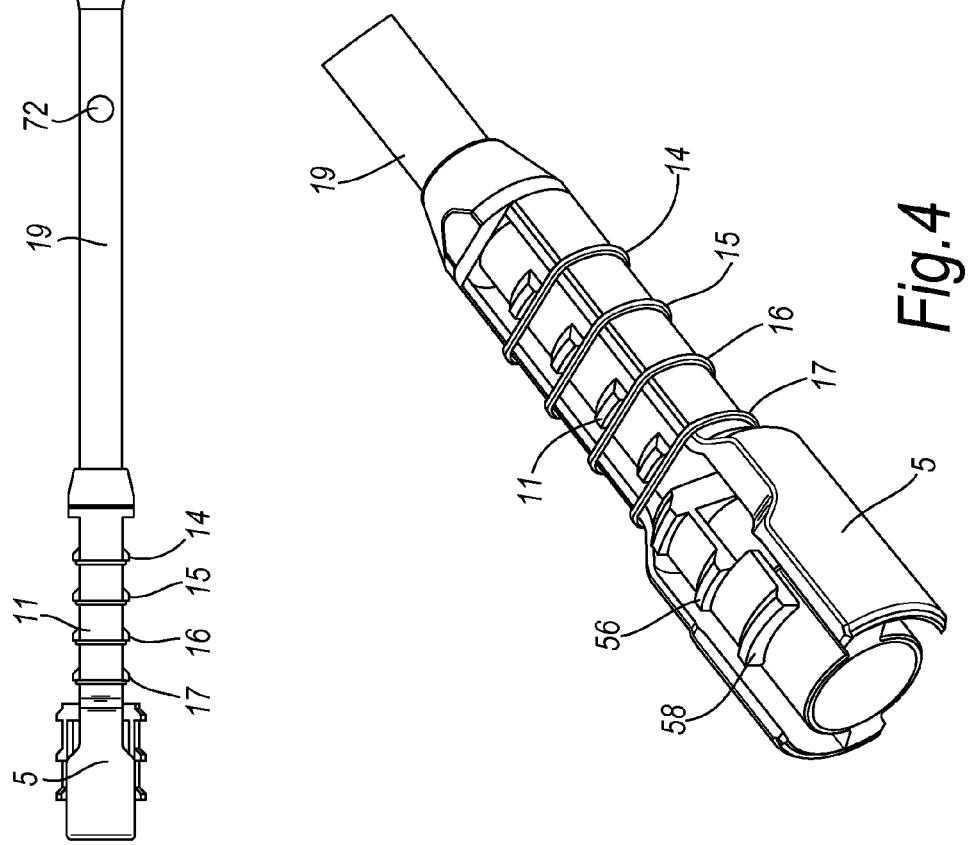

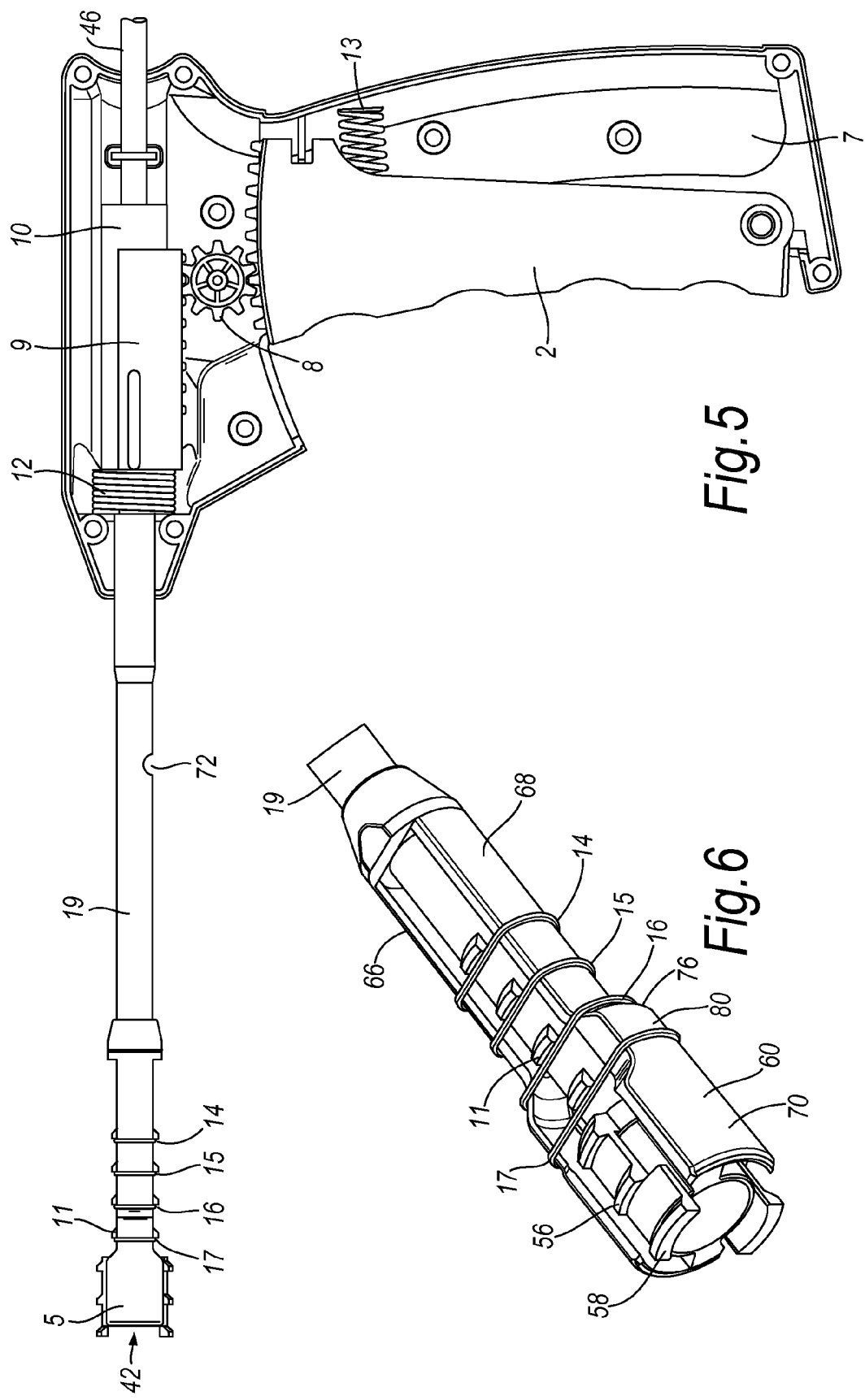

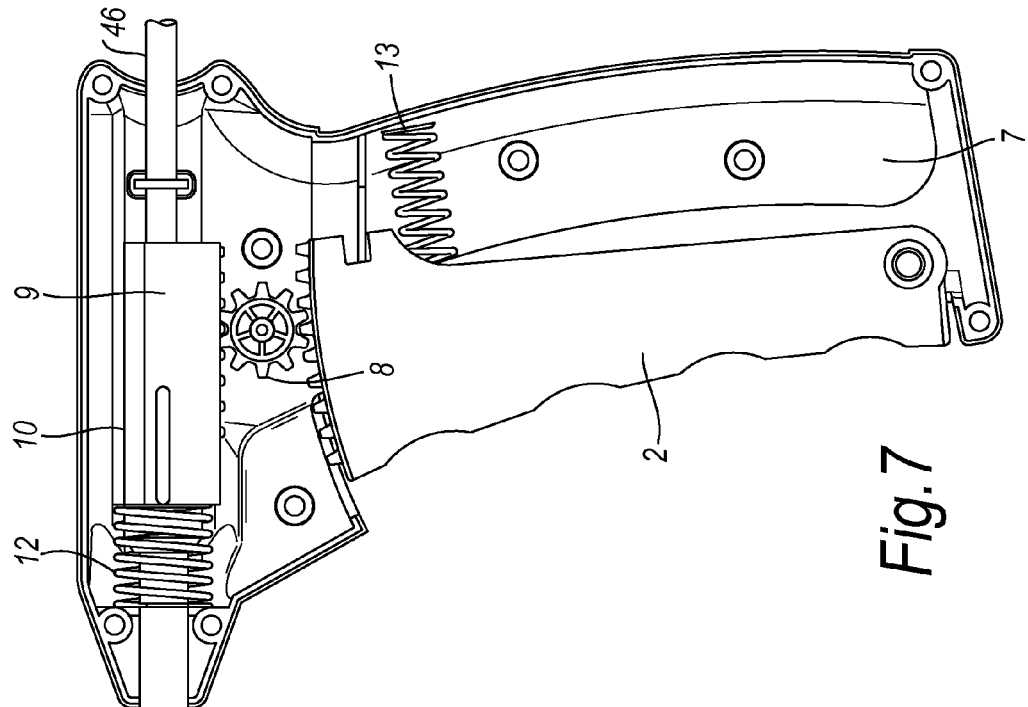
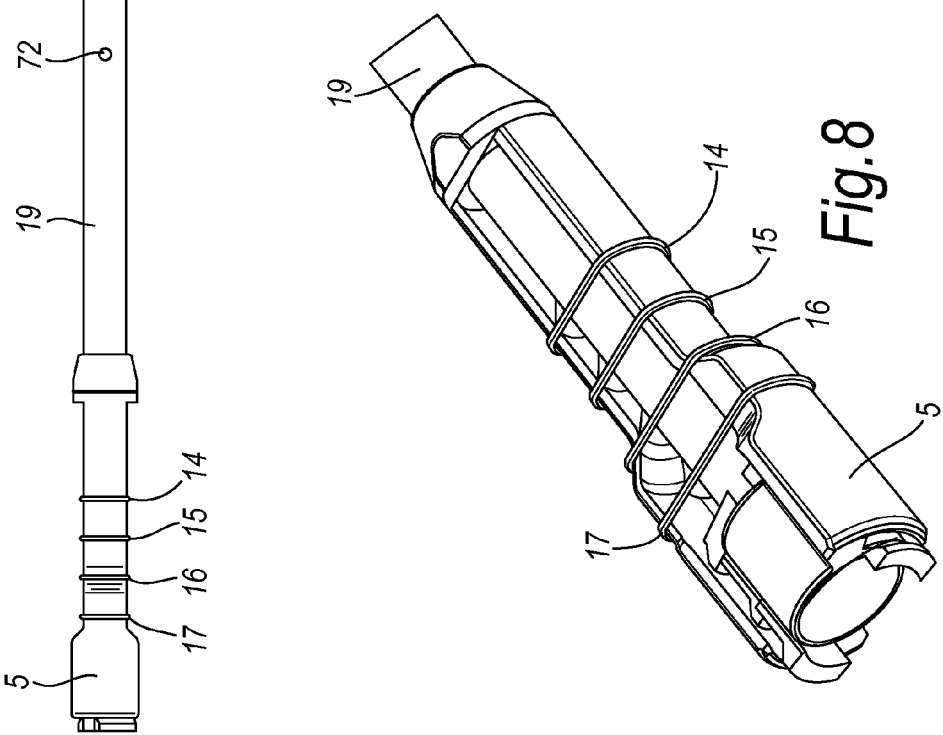

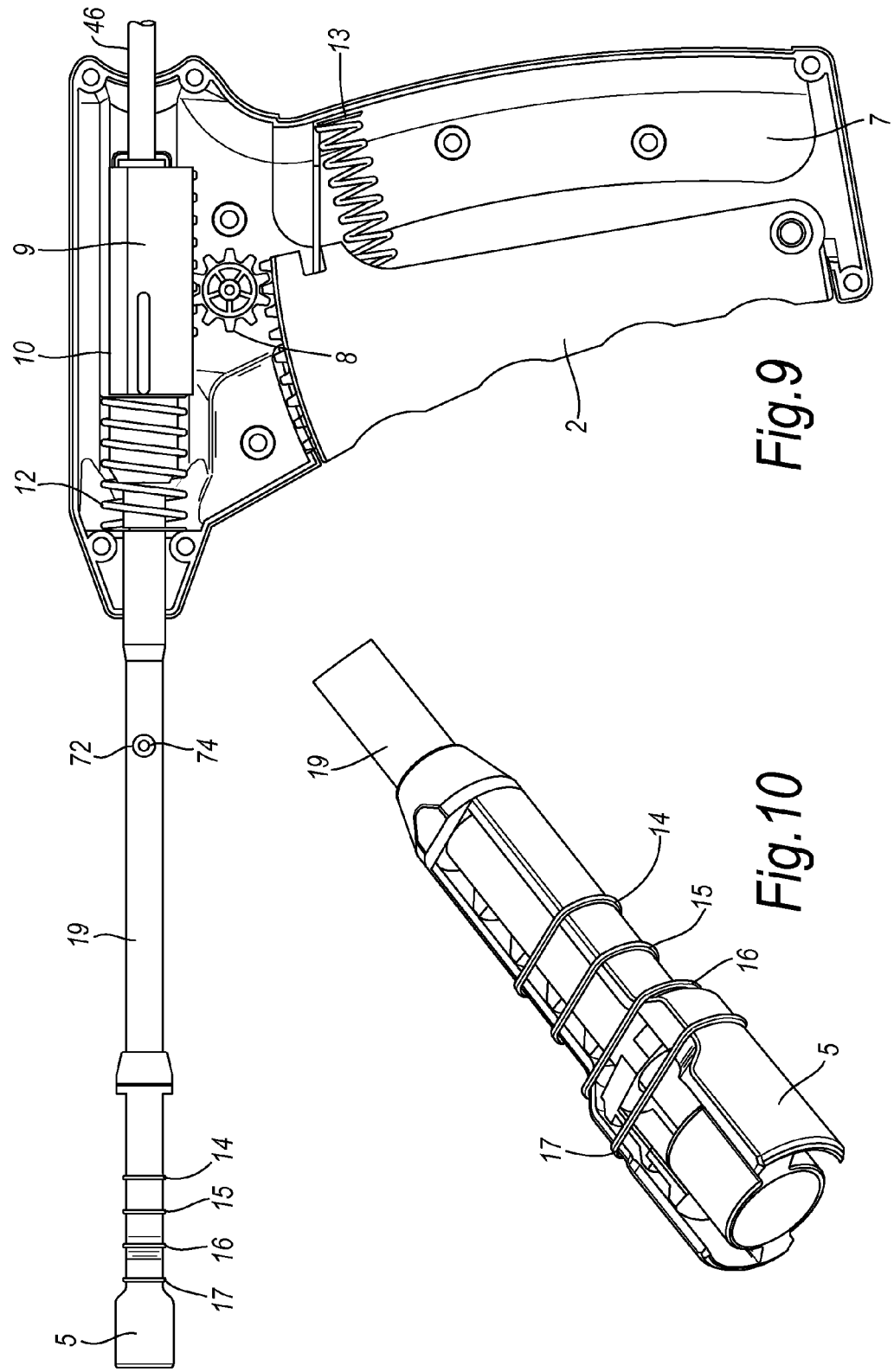

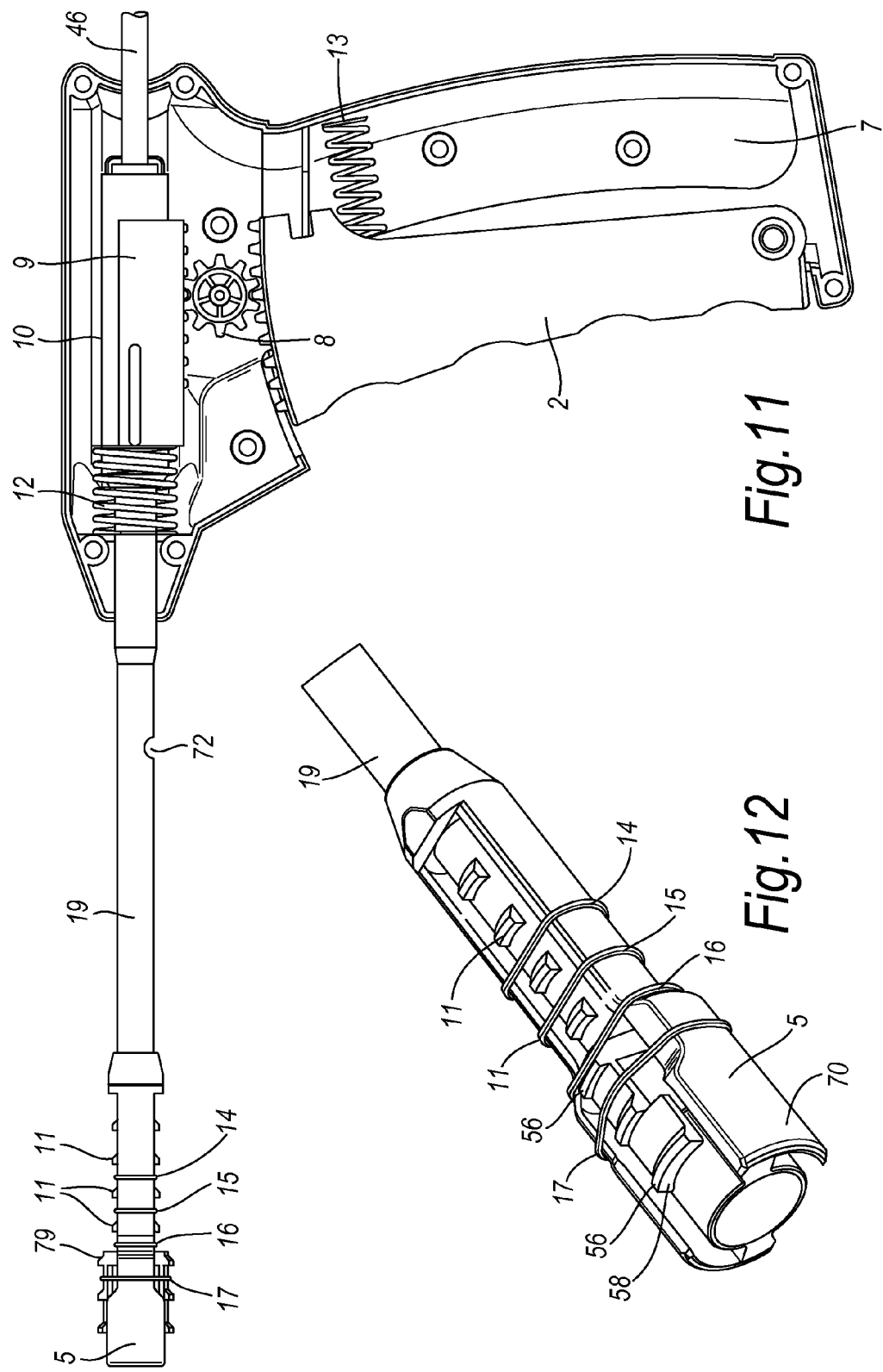

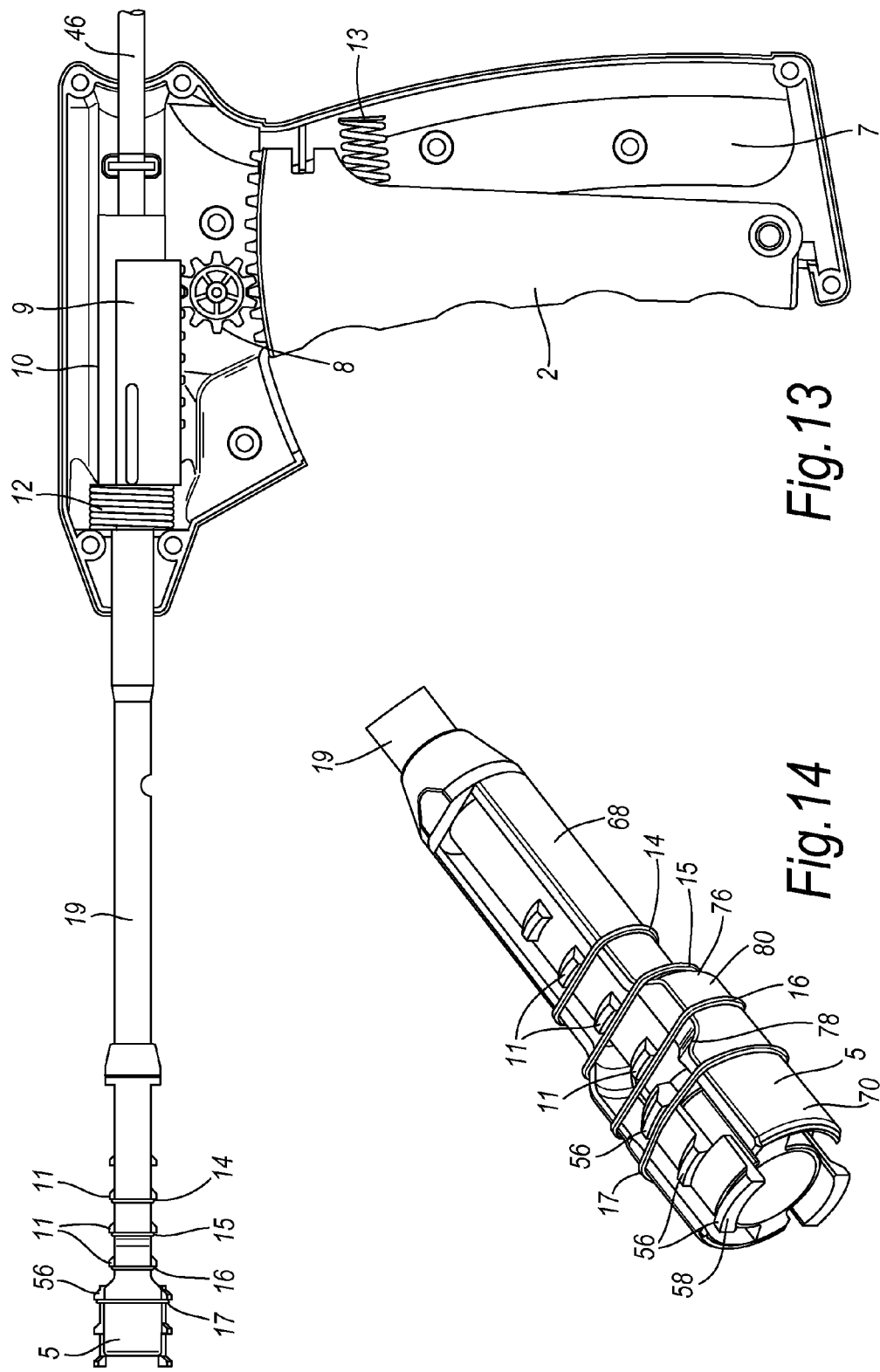

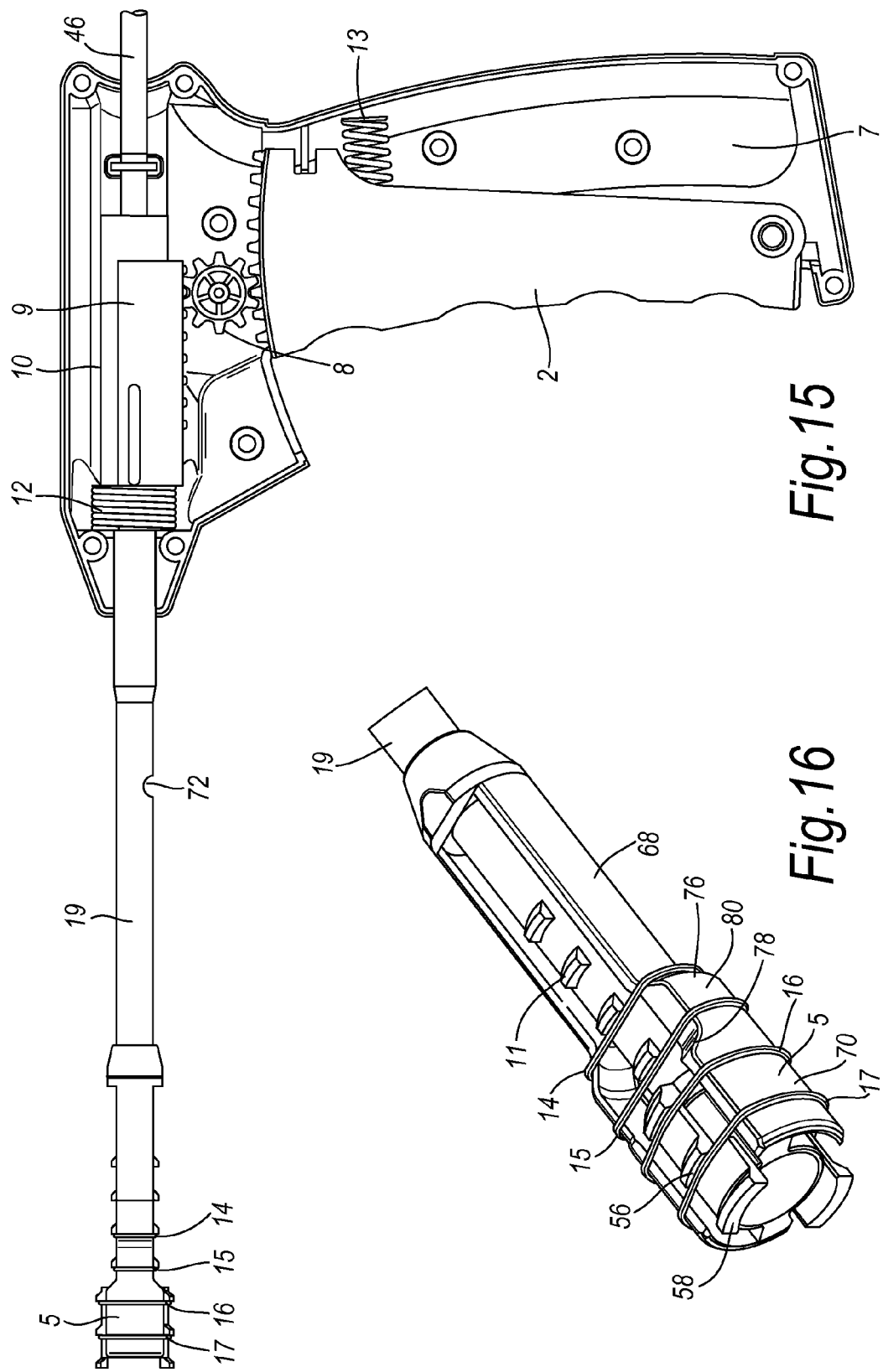

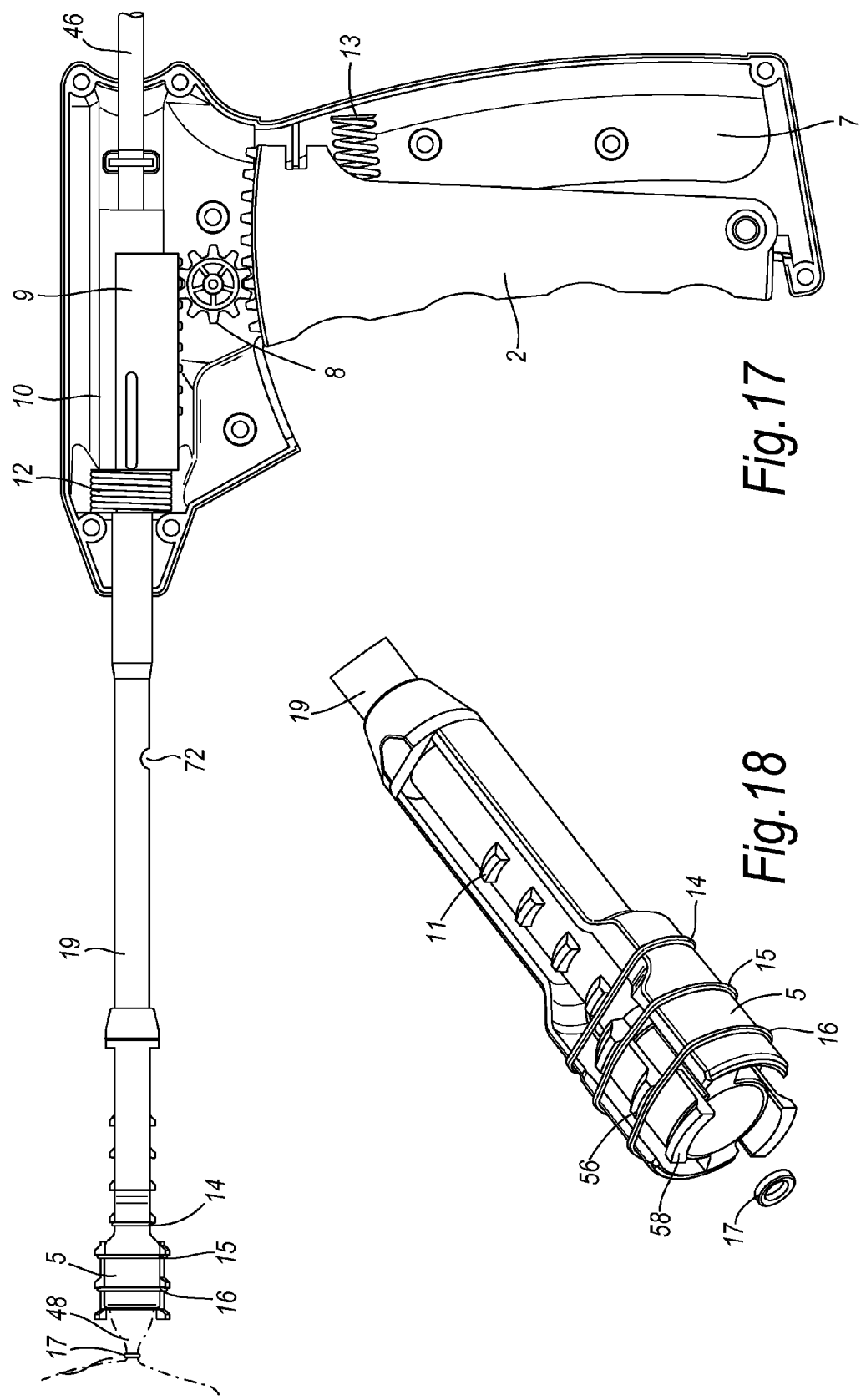

DEVICE FOR APPLYING SUCCESSIVE RESILIENT LIGATING BANDS TO TISSUE

FIELD OF THE INVENTION

The present invention relates to a ligating instrument for ligating tissue, especially for ligating a plurality of varices such as haemorrhoids (piles).

BACKGROUND TO THE INVENTION

Haemorrhoids are one of the most common surgical diseases around the world. Various methods of treatment have been developed. The least expensive and most widely used method is rubber band ligation. It has been in use for many years and has proved to be the most effective.

In the known technique, a relatively long forceps is employed to hold the hemorrhoid, which is pulled through an O-ring forceps with a relatively long arm. The external part of the O-ring holds an already stretched rubber band. Once the forceps has grasped the hemorrhoid, the rubber band is fired from the O-ring by a simple pushing mechanism. The problems with the known technique include the requirement for two people to perform it, one to hold the anoscope and the other to apply the bands. This anoscope is needed to be able to visualize the haemorrhoids.

Because it is necessary to have two people to perform the technique, misfiring of the bands is frequent and readjustment is therefore required. Sterilization of the equipment between patients is essential, so many sets are needed.

As each patient usually needs 2 or 3 rubber bands to be applied, the O-ring must be loaded each time with a fresh band, which is a demanding task. Thus the O-ring forceps must be removed while maintaining the anoscope inside the patient, significantly extending the procedure time and requiring prolonged handling when contaminated.

A less common condition called oesophageal varices, which is dilated veins at the lower part of the oesophagus, is treated endoscopically in a similar way by applying rubber bands to the varices. One known endoscopic ligating instrument for this purpose was disclosed in 1998 in U.S. Pat. No. 4,735,194 (Stiegmann). The disclosed endoscopic ligating instrument has an outer tube mounted on the tip end of an endoscope and an inner tube axially movably inserted in the outer tube. A trip wire has an end coupled to the inner tube, extends through a biopsy channel, and has an opposite end projecting out of the endoscope and joined to a handle. When the handle is pulled, the trip wire is axially moved to move the inner tube rearwardly into the outer tube. A ligating O-ring made of an elastomeric material is expanded radially outwardly and mounted on a tip end of the inner tube which projects out of the front end of the outer tube.

The endoscopic ligating instrument is used as follows. The endoscope is inserted into the esophagus, for example, of a patient until the tip end of the inner tube covers a varix to be ligated. Then, after a region where the varix exists is drawn into the inner tube under suction or the like, the handle is pulled to move the inner tube rearwardly into the outer tube. The ligating O-ring is now pushed off the inner tube by the tip end of the outer tube, and contracted radially inwardly, thereby ligating the base of the target lesion. Since the blood flow to the ligated varix is blocked, the ligated varix hardens and may be removed. The removal of the ligated varix finishes the treatment of the patient.

However, since only one ligating O-ring is mounted on the inner tube, if a plurality of varices are to be ligated successively, then it is necessary, each time a varix has been removed, to take the endoscope out of the cavity, replace the inner tube with a new inner tube with a ligating O-ring mounted thereon, and then insert the endoscope back into the cavity for ligating treatment. For ligating a plurality of varices, therefore, the endoscope is required to be inserted into and taken out of the cavity as many times as the number of varices to be ligated. Such a ligating practice can cause considerable pain to the patient.

Another known endoscopic ligating instrument was disclosed in 1994 and 1995 in U.S. Pat. No. 5,320,630, U.S. Pat. No. 5,462,559 and U.S. Pat. No. 5,624,453 (Ahmed/Wilson Cook Medical). The device has been further adapted to provide a means of mucosal resection via rubber band ligation. This treatment has proved its efficiency in stopping bleeding from oesophageal varices. The rubber bands are loaded on a cartridge, which is loaded on the tip of a flexible fibre optic gastroscope. This is passed down into the patients' esophagus and the rubber bands are applied on the varices, which are drawn into the cartridge by the means of suction. The mechanisms used to fire the rubber bands are dependent on a thread applied over the cartridge body, under the rubber bands. Drawing the thread will fire the rubber bands. A plurality of rubber bands can be fired using this method. The same mechanism has been adapted to treat haemorroids in the Saeed ShortShot (ex Cook Medical).

The problem with this method is that time and a complex effort are needed to assemble the cartridges. That makes them expensive.

In 1995, European patent publication EP 0679368 (Hosoda) described an endoscopic ligating instrument for ligating varix. The instrument has an outer tube having a rear end in which the tip end of an endoscope is mounted. An inner tube with a trip wire connected thereto is axially movably inserted in the outer tube. When the inner tube is moved rearwardly, the inner tube is urged to move forwardly by a spring. Three ligating O-rings are mounted respectively at axially equally spaced positions on the outer circumferential surface of a portion of the inner tube which projects from the outer tube. Four arms extending forwardly from the outer tube are disposed respectively at circumferentially equally spaced positions over the outer circumferential surface of the inner tube. Each of the arms has teeth disposed behind the ligating O-rings, respectively, and having front pushing surfaces for pushing the ligating O-rings forwardly when the inner tube is moved rearwardly and rear slant surfaces for riding over the ligating O-rings and spreading the arms radially outwardly when the inner tube is moved forwardly. The endoscopic ligating instrument can ligate a plurality of varices successively when the endoscope is inserted in a cavity in the body of a patient.

In 2003 International patent publication WO 2003/099141 (Ghareeb) described a ligating device for applying successive elastic bands to tissue. In one preferred embodiment, the device includes a barrel having an opening into which the tissue can be drawn and a plurality of circumferential grooves around the barrel each for accommodating a respective ligating band. The grooves may be defined by ridges on first and second coaxial tubes respectively, the second tube being reciprocal relative to the first tube so that when the second tube advances towards the front end of the barrel its ridges push the bands forwardly so that they ride up over the ridges of the first tube to each lie one groove nearer the front end, the foremost band being pushed off the front end of the first tube onto the tissue. When the second tube retracts away from the front end the bands ride up over the ridges of the second tube to remain in their advanced positions.

In 2006, United States patent publication US 2006/259042 (Ali Hassanien) described a device for multi-ligation of veins of the haemorrhoid which comprises a front part including a fixed pipe surrounded by a movable pipe, a triggering cylinder with a triggering handle of elongated cylinder construction connected between the rear of a third part and the front part, and the third part being a rear part or mechanical handle part comprising a cylinder and handle for holding the device and a mechanism including the handle for effecting suction of veins into the front part of the device by pulling the handle with a connected piston backward.

Also in 2006, British patent publication GB 2426459 (Mihssin) described a single use haemorrhoid multi rubber band firing device which delivers up to four rubber bands in one application. The device may comprise an inner tube with four bands mounted at one end, an outer tube, a rotating spool, suction source and a suction port which may be blocked by a finger. The bands may be advanced by rotating the spool over a threaded part of the inner tube to advance the outer tube. The contact area between the bands and the outer tube may be lessened to reduce friction. The rubber band may have four protrusions on one side or it may be doughnut shaped to reduce contact with the inner tube and act as spacers between the bands.

The device described in WO 2003/099141 (Ghareeb) above has had some commercial use. However, the Ghareeb device suffers from a number of disadvantages. The ligating bands are all pre-stretched to a wide diameter which, when left in this state for a period of time, impairs the capacity of the band to return to the original internal diameter which it had prior to loading on the device. This in turn impairs the capacity of the band to satisfactorily ligate tissue, with the band either falling off prematurely or not achieving the desired effect on the tissue. Furthermore, the end of the device is comparatively large, obscuring the view through the proctoscope of the practitioner when applying the bands. The delivery of the bands can be unreliable, particularly once a lubrication gel has been applied, because the pusher teeth can slip under the bands and not fire the end band or advance the successive bands into the next circumferential groove.

The Mihssin device described above also suffers from a number of disadvantages, primarily that the bands are not satisfactorily spaced and frequently fire multiple bands at once.

The Saeed ShortShot ligator, requiring the use of threads to dispense the bands has similar problems to the Ghareeb and Mihssin devices in that the threads often do not progress the ligating bands in a uniform manner with the result that either no band or multiple bands are fired with a single shot.

The present invention enables the provision of a device for applying successive resilient ligating bands to tissue in a manner which reduces or overcomes the disadvantages of the prior art devices.

SUMMARY OF THE INVENTION

According to a first aspect of the present invention, there is provided a device for applying successive resilient ligating bands to tissue, the device comprising:
a) a sleeve having an opening at a front end thereof, the sleeve having a plurality of axially extending arms having axially extending spaces therebetween, and band-support surfaces located on the arms extending from the front end for accommodating a plurality of ligating bands;
b) a first tube around which the sleeve is located, the first tube being reciprocal relative to the sleeve in the direction towards and away from the front of the device, the first tube having a at least one axially extending finger provided with a plurality of forward-facing pushing surfaces;
c) means for drawing tissue to be ligated into the opening;
d) drive means for driving the first tube relative to the sleeve from a rest position along a first movement path including
(i) a rotational component to bring the finger(s) from a rest position into alignment with the axially extending spaces between the arms, and
(ii) a subsequent axial component to advance the first tube towards the front end of the sleeve thereby to cause the pushing surfaces to push the bands forwardly so that they ride along the band-support surfaces of the sleeve to each lie nearer the front end, the foremost band being pushed off the front end of the sleeve onto the tissue; and
e) drive means for returning the first tube to its rest position along a second movement path comprising
(i) a rotational component to bring the finger(s) behind the arms, and
(ii) a subsequent axial component to retract the finger(s) into their rest position.

By mounting the ligating bands on the sleeve, the sleeve having arms with spaces therebetween, the bands occupy a non-circular, e.g. oval configuration. This configuration of the bands enables the finger(s) on the first tube to rotate from a rest position to lie inwards of the sleeve arms to a position to contact the bands, with the pushing surfaces able to push against the rear edges of the bands as the finger(s) subsequently move forward. This non-circular configuration of the bands is in contrast to the circular configuration adopted by the bands in the devices described in the prior art documents referred to above.

Preferably, the first tube is of circular cross section. The sleeve is preferably of circular cross-section and located concentrically with respect to the first tube. Preferably, a plurality of the fingers are provided. The fingers ideally each subtend at the tube axis an angle no greater than that subtended by the arms.

The plurality of fingers and/or the plurality of arms are preferably symmetrically spaced about the tube axis.

In a preferred embodiment, the number of fingers is equal to the number of arms. For example, two fingers and two arms are provided. The fingers may be of identical length, but more preferably one finger extends fully to the forward end of the outer tube while the other finger stops short of that forward end. By providing fingers of different length, a larger pushing surface is available on the shorter finger for pushing a band up on to the forward region of the sleeve.

The sleeve is preferably connected to a second tube positioned within the first tube, the first or outer tube being capable of sliding and rotational movement relative to said second or inner tube.

The pushing surfaces are provided on the finger(s) and preferably also on the first tube. The pushing surfaces are preferably comprised of a plurality of axially spaced teeth mounted on the finger(s), and optionally additionally on the first tube immediately to the rear of the finger(s). The teeth on the finger(s) are preferably arranged in an axial line, which are preferably aligned with an axial line of teeth on the first tube. The number of teeth will be determined by the number of ligating bands with which the device is intended to be used.

The drive means for driving the first tube relative to the sleeve along the first movement path may include a cam guide, the shape of the cam guide defining the first movement path. Similarly, the drive means for driving the first tube relative to the sleeve along the second movement path may include a cam guide, the shape of the cam guide defining the second movement path. Ideally, the same cam guide defines both movement paths.

The drive means for driving the first tube relative to the sleeve may include a manually operable actuator, such as a trigger.

According to a second aspect of the invention, there is provided device for applying resilient ligating bands to tissue, the device comprising:
a) a sleeve having an opening at a front end thereof,
b) means for drawing tissue to be ligated into the opening, and
c) band-supporting surfaces around the sleeve extending from the front end each for accommodating one or more ligating bands,
d) a first tube having forward facing pushing surfaces, the first tube being reciprocal relative to the sleeve in the direction towards and away from the front end of the sleeve, and
e) drive means for advancing the first tube towards the front end so that its pushing surfaces push the bands forwardly to each lie nearer the front end, the foremost band being pushed off the front end of the sleeve onto the tissue,
wherein the sleeve has a region of smaller dimension remote from the front end, at least part of said band-support surfaces being located in said smaller dimension region, the smaller dimension region merging with a larger dimension region by way of a transition portion having a progressively increasing dimension in the direction towards the front end.

In the second aspect of the device, the dimension of the sleeve which varies is the diameter of the band-supporting surfaces of the sleeve and/or the circumference of the band-supporting surfaces of the sleeve.

In a preferred embodiment, the sleeve has a region of smaller diameter remote from the front end, at least part of the band-support surfaces being located in the smaller diameter region. The region of smaller diameter preferably merges with the region of larger diameter which is nearer the front end by way of a transition portion having a progressively increasing diameter in the direction towards the front end. As an additional or alternative feature, the arms of the sleeve each have a region of smaller circumference remote from the front end, at least part of the band-support surfaces being located in the smaller circumference region. The region of smaller circumference preferably merges with the region of larger circumference which is nearer the front end by way of a transition portion having a progressively increasing circumference in the direction towards the front end. By use of these features, the bands are not in an excessively stretched condition, while the device is waiting to be used, and can be progressively stretched as they are advanced towards the front end.

Where the sleeve is mounted on a second tube, as referred to above, the means for drawing tissue into the opening preferably comprises means for establishing a reduced air pressure in the opening via the second tube, such as a suction pipe connectable to the second tube. In a preferred embodiment, the device may be adapted such that reduced air pressure is established at the opening as the first tube is driven along the first movement path and is disestablished at the opening in the rest position. This may be achieved wherein the second tube has an aperture in a side wall thereof aligned with an aperture in a side wall of the first tube when the device is in its rest position. These apertures may, for example, each be circular holes or circumferential slots. In this manner, the vacuum can be applied automatically, but is not applied to the opening while the device is being inserted or withdrawn from the patient's body.

In a preferred embodiment, the tissue comprises a hemorrhoid.

The device may be formed of any suitable material including metals and plastics materials, and the components of the device may be formed by any suitable process, such as by moulding. The sleeve should be sufficiently rigid so as not to be distorted by the stretched ligating bands mounted thereon to the extent to prevent the device from operating as intended. For example, the sleeve may be more rigid than the first tube or other components of the device. The ligating bands may be formed of any suitable resilient material such as natural or synthetic rubber, as already known in the art.

Thus, the device according to embodiments of the present invention provides a secure and reliable means of dispensing successive bands in a uniform way, without the need to excessively pre-stretch them, while maximising the view for the practitioner.

BRIEF DESCRIPTION OF THE DRAWINGS

The invention will now be further described, purely by way of example, with reference to the accompanying drawings, in which:

FIG. 1 shows a device according to the invention, in its rest position;

FIG. 2 shows the forward end of the device shown in FIG. 1, also in its rest position;

FIG. 3 shows the device after a partial first actuation of its trigger, but with part of the housing of the device removed to clarify the view of the internal construction;

FIG. 4 shows the forward end of the device, also after a partial first actuation of its trigger;

FIGS. 5 and 6 are similar to FIGS. 3 and 4, but show the position after full actuation of the trigger;

FIGS. 7 and 8 are similar to FIGS. 3 and 4, but show the position after partial release of the trigger;

FIGS. 9 and 10 are similar to FIGS. 3 and 4, but show the position after full release of the trigger;

FIGS. 11 and 12 are similar to FIGS. 3 and 4, but show the position after a partial second actuation of the trigger;

FIGS. 13 and 14 are similar to FIGS. 5 and 6, but show the position after full second actuation of the trigger;

FIGS. 15 and 16 are similar to FIGS. 13 and 14, but show the position after full third actuation of the trigger;

FIGS. 17 and 18 are similar to FIGS. 15 and 16, but show the position after full fourth actuation of the trigger;

DESCRIPTION OF A PREFERRED EMBODIMENT

Figure 19:
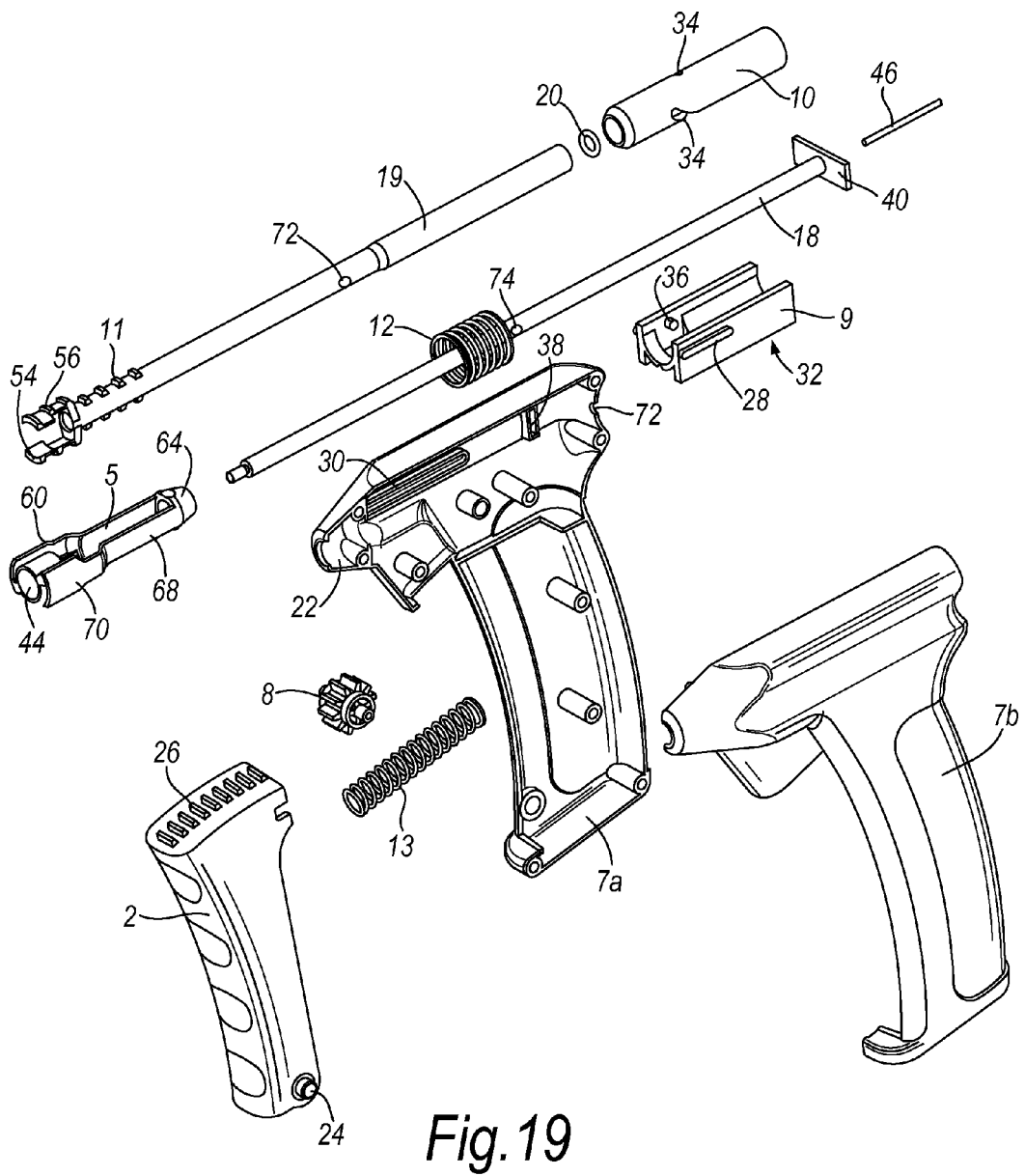
FIG. 19 is an exploded view of the device shown in FIGS. 1 to 18.

Referring to the drawings, there is shown a device 1 for applying successive resilient ligating bands to a haemorrhoid. The device shown in the drawings is mainly formed of moulded polystyrene and includes a housing 7 made up of right and left parts 7a, 7b which are connected together by adhesive or other suitable means. The housing has a generally pistol-like shape with a handle part 7c and a barrel part 7d with a nozzle 22. A trigger 2 is mounted within the handle part 7c of the housing 7 at pivot 24 and is urged by a spring 13 in a forwards direction. The top edge of the trigger 2 carries a toothed rack 26, which engages a gear wheel 8 mounted for rotation within the housing 7.

Figure 20:
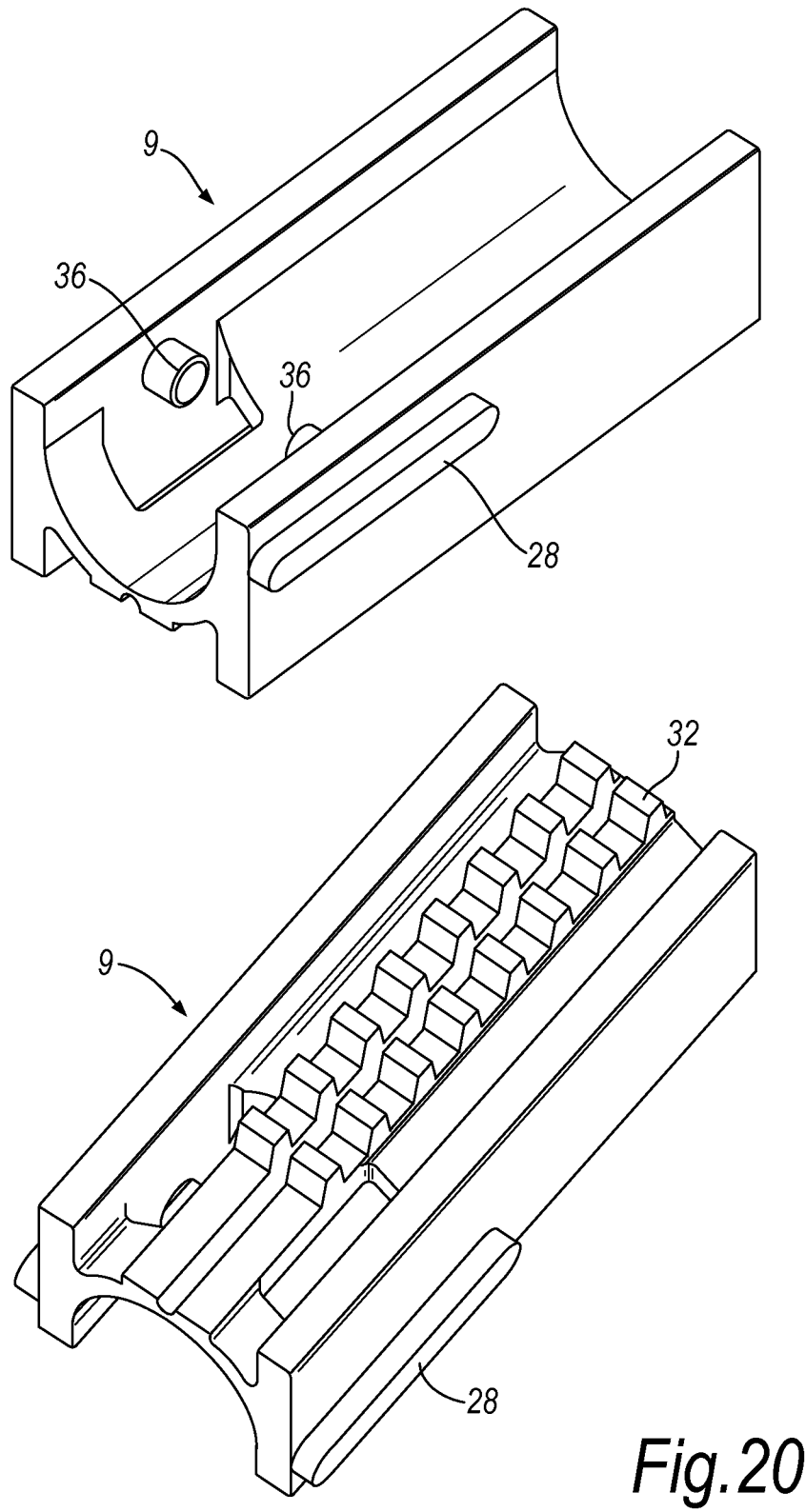
FIG. 20 shows detailed views of the cradle of the device shown in FIGS. 1 to 19, viewed from above and below.

A cradle 9 is mounted within the housing 7 for reciprocal forward and rearward movement by the engagement of lugs 28 in closed ended guide slots 30 formed within the barrel part 7*d* of the housing 7. The underside of the cradle 9 carries a gear rack 32 (see especially FIG. 20) which engages the gear wheel 8. The limits of movement of the cradle 9 are determined by the length of the guide slots 30.

Figure 21:
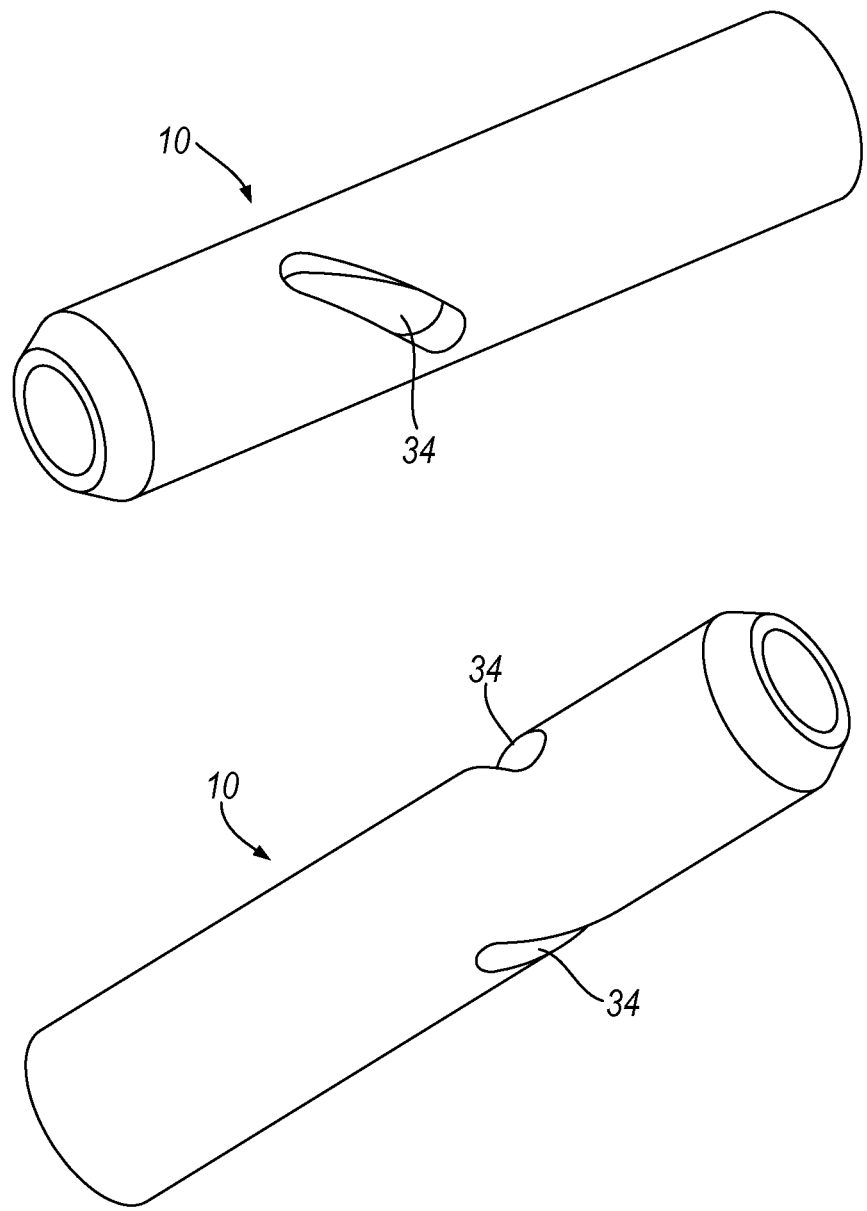
FIG. 21 show detailed views of the roller of the device shown in FIGS. 1 to 19.

A hollow roller 10 sits in the cradle 9. The circumferential face of the roller 10 (see especially FIG. 21) is provided with two closed ended helical cam slots 34 which are engaged by cam pins 36 formed on the roller-supporting surface of the cradle 9. The rear end of a first hollow tube 19 of circular cross section is carried within the roller 10 and by way of a O-ring 20 is a tight fit therein. The outer tube 19 passes out through the forward end of the barrel part 7*d* of the housing 7.

The housing parts 7*a*, 7*b* each have a recess 38 which jointly accommodate a plate 40 secured on the rear end of a second hollow tube 18 of circular cross section, the forward end of which passes through the outer tube 19 and out of the barrel part 7*d* of the housing 7. The inner tube 18 is reciprocal relative to the outer tube 19 in the direction towards and away from the front end 42 of the device and has an opening 44 at its front end 42. A suction line 46, passing through an aperture 73 in the barrel part 7*d* of the housing 7, is connected to the inner tube 18 for drawing the haemorrhoid 48 to be ligated towards the front end 42 of the sleeve 60 and into the opening 44.

The trigger 2, gear wheel 8, cradle 9 and roller 10 together constitute a drive mechanism 50 for driving the outer tube 19 relative to the inner tube 18 along first and second movement paths. The arrangement is such that pivoting of the trigger 2, against the force of the spring 13, causes the gear wheel 8 to rotate in one rotational direction which in turn drives the cradle 9 in a forward direction, against the force of a spring 12 extending between the cradle 9 and the nozzle 22 of the housing 7. As the cradle 9 moves forward, the cam pins 36 ride along the cam slots 34 in the roller 10, causing the roller and the outer tube 19 to rotate in one rotational direction. After a roller rotation of about 90° about the tube axis 52, the cam pins 36 reach the forward ends of the cam slots 34, so that further forward movement of the cradle drives the roller and the outer tube 19 forwards, without further rotation. The O-ring 20 serves to ensure that the forward movement of the cradle 9 causes the outer tube 19 to rotate before causing it to advance. This is the first movement path.

When the trigger is released, and returns to its rest position under the force of the spring 13, the gear wheel 8 is caused to rotate in the opposite rotational direction which in turn drives the cradle 9 in the rearward direction, as urged by the spring 12. As the cradle 9 moves rearwardly, the cam pins 36 ride back along the cam slots 34 in the roller 10, causing the roller and the outer tube 19 to rotate in the opposite rotational direction. After a roller rotation of about 90° about the tube axis 52, the cam pins 36 reach the rear ends of the cam slots 34, so that further rearward movement of the cradle drives the roller and the outer tube 19 rearwardly, without further rotation. This is the second movement path.

At the forward end of the outer tube 19, there are two fingers 54 symmetrically circumferentially spaced about the common tube axis 52. The fingers 54 describe parts of the circumference of a circle having a diameter greater than the outer diameter of the outer tube 19. Each of the fingers 54 subtends an angle of about 85° at the axis 52 of the outer tube 19. Two lines of axially spaced teeth are provided on the fingers 54 and at the adjacent front end of the outer tube 19 with three teeth 56 on each of the fingers 54 and two lines of four teeth 11 on the outer tube 19 immediately to the rear of the fingers 54. Each of the teeth 11, 56 has a forward-facing pushing surface 58. The front end of the inner tube 18 is secured to a band-support member in the form of a sleeve 60 of circular cross-section, the sleeve being formed of stainless steel or a steel replacement plastics material, having a rigidity greater than that of the moulded polystyrene of which the other components of the device are formed. The sleeve 60 is formed with two circumferentially spaced apart arms 5, located to the left and right of the device, the arms 5 having axially extending spaces 62 therebetween, located on top of and below the sleeve 60. The sleeve 60 accommodates a number of rubber ligating bands 14, 15, 16, 17, each stretched into a generally oval configuration. The arms 5 extend rearwardly to a frusto-conically shaped collar 64 which surrounds the inner and outer tubes 18 and 19 and is a sliding fit thereon. Each of the arms 5 subtends an angle of about 85° at the axis 52 of the outer inner tube 18 so that, in the rest position, the arms 5 completely cover the fingers 54 and the associated teeth 56 as well as the teeth 11 on the outer tube 19, i.e. the fingers 54 and the teeth 56 and 11 do not protrude into the spaces 62.

Each of the arms 5 defines a part-cylindrical surface 66 having three regions, a rearward region 68 of relatively narrow diameter where the arms 5 have a relatively shorter circumference, a forward region 70 of relatively wider diameter where the arms 5 have a relatively longer circumference, an intermediate region 80 having the same circumference as the rearward region 68 and the same diameter as the forward region 70. The intermediate region 80 is located between a transition portion 76 of progressively larger diameter and a transition portion 78 where the arms 5 have a progressively longer circumference. By use of these features, the bands are not in an excessively stretched condition, while the device is waiting to be used, and can be stretched in two steps as they are advanced towards the front end.

The drive mechanism described above is arranged such that the first movement path includes a rotational component to initially bring the inner fingers 54 with the associated teeth 56 as well as the teeth 11 on the outer tube 19, from a rest position into alignment with the axially extending spaces 62 between the arms 5, and a subsequent axial component to advance the fingers in a forward direction relative to the sleeve 60. The drive mechanism is also arranged such that the second movement path includes an initial rotational component to bring the inner fingers 54 with the associated teeth 56 as well as the teeth 11 on the outer tube 19, behind the outer arms 5 and a subsequent axial component to retract the inner fingers 54 into their rest position.

In the initial rest position shown in FIG. 2, a number of ligating bands are mounted in spaced apart relationship on the narrow diameter region of the sleeve 60. In the rest position, the fingers 54 on the outer tube 19 and the associated teeth 56 as well as the teeth 11 on the outer tube 19, are located behind the arms 5 of the sleeve 60.

In the position shown in FIGS. 3 and 4, after a partial first actuation of the trigger 2, the outer tube 19 has rotated through about 90° in an anticlockwise direction (as viewed from the rear of the device) about the axis 52 to bring the fingers 54 from the rest position into alignment with the axially extending spaces 62 between the arms 5. This movement brings the teeth 11 into position behind, respectively, the bands 14, 15, 16 and 17.

In the position shown in FIGS. 5 and 6, after full actuation of the trigger 2, an axial movement to advance the outer tube 19 towards the front end 42 of the sleeve 60 causes the pushing surfaces 58 on the teeth 11 to push the bands 14, 15, 16, 17 forwardly so that they ride along the part-cylindrical band-support surfaces 66 of the sleeve 60 to each lie nearer the front end 42. The foremost band 17 is pushed from the relatively narrow rearward region 68 onto the wider intermediate region 80 via the transition portion 76 of progressively increasing diameter, thereby partly expanding the band.

In the position shown in FIGS. 7 and 8 after partial release of the trigger 2, the hollow outer tube 19 has rotated clockwise by about 90° about the axis 52 to bring the fingers 54 back behind the arms 5, and thereby to release any contact between the teeth 11 and the bands 14 to 17.

In the position shown in FIGS. 9 and 10 after full release of the trigger 2, the outer tube 19 has withdrawn to retract the fingers 54 into their rest position as shown in FIGS. 1 and 2, save that the bands 14 to 17 have advanced along the sleeve 60.

FIGS. 11 and 12 show that after a partial second actuation of the trigger 2, the outer tube 19 has again rotated anticlockwise through about 90° about the axis 52 to bring the fingers 54 from the rest position into alignment with the axially extending spaces 62 between the arms 5. This movement brings the teeth 11 into position behind the bands 14, 15, 16 and the rearmost of the teeth 56 behind the band 17.

After completion of the second actuation of the trigger 2, as shown in FIGS. 13 and 14, axial movement to advance the outer tube 19 towards the front end 42 of the sleeve 60 has caused the pushing surfaces 58 on the teeth 11 and 56 to push the bands 14 to 17 forwardly so that they ride along the part-cylindrical band-support surfaces 66 of the sleeve 60 to each lie nearer the front end 42. The second-most band 16 has been pushed from the relatively narrow rearward region 68 onto the wider intermediate region 80 via the transition portion 76, thereby expanding that band in lateral directions. Also, the first-most band 17 has been pushed from the intermediate region 80 via the transition portion 78 of increasing circumference to the larger dimensioned forward region 70, thereby further expanding the band in all radial directions, into an almost circular configuration.

The position after a full third actuation of the trigger 2 is shown in FIGS. 15 and 16. The outer tube 19 has again rotated anticlockwise through about 90° about the axis 52 to bring the fingers 54 from the rest position into alignment with the axially extending spaces 62 between the arms 5. This movement has brought the teeth 11 into position behind the bands 14 and 15 and teeth 56 behind the bands 16 and 17. After completion of this third actuation of the trigger 2, axial movement to advance the outer tube 19 towards the front end 42 of the sleeve 60 has caused the pushing surfaces 58 on the teeth 11 and 56 to again push the bands 14 to 17 forwardly so that they ride along the part-cylindrical band-support surfaces 66 of the sleeve 60 to each lie nearer the front end 42. The third-most band 15 has been pushed from the relatively narrow rearward region 68 onto the wider intermediate region 80 via the transition portion 76, thereby laterally expanding that band, while the second-most band 16 has been pushed from the intermediate region 80 via the transition portion 78 to the larger dimensioned forward region 70, to join the first-most band 17.

The device is now ready for patient treatment. A vacuum is connected to the suction tube 46 and the front end of the device is introduced into the anus of the patient to be treated through the use of an anoscope to treat, for example, haemorrhoids. In the rest position, the circular holes 72 and 74 are aligned, so that the vacuum is not applied to the opening 44.

The trigger 2 is now actuated to bring the device into the position shown in FIGS. 17 and 18. The outer tube 19 has again rotated anticlockwise through about 90°. The movement of the outer tube 19 has brought the circular holes 72 and 74 out of alignment with each other, i.e. the circular hole 74 has become occluded, so that the vacuum is now applied to the opening 44 and the hemorrhoid 48 is drawn into the opening 44. In an alternative embodiment, the circular holes 72 and/or 74 may be in the form of circumferential slots, so that the vacuum is applied to the opening 44 only when the outer tube 19 is advanced towards the front end 42 of the device.

Returning to the illustrated embodiment, the fingers 54 have again been brought from the rest position into alignment with the axially extending spaces 62 between the arms 5, to bring the forward-most one of the teeth 11 into position behind the band 14 and teeth 56 behind the bands 15 and 16. The foremost band 17 has been pushed off the front end 42 of the sleeve 60 onto the hemorrhoid 48 and retracts around the hemorrhoid. Release of the trigger 2 returns the device to its rest position as described above.

If desired by the operator, another actuation of the trigger 2 will apply the next band, 16, to the same haemorrhoid, or alternatively the next band 16 can be applied to another haemorrhoid. In either case, it is unnecessary for the device to be removed from the patient or re-loaded between each band application.

While the device shown in the drawings and described in detail herein, has been loaded with four bands, more or fewer bands could be loaded onto the device.

The operating process is repeated until the desired number of ligating bands have been pushed off the front end 42 of the sleeve 60 by the outer tube 19 onto the hemorrhoid 48.

Figure 22:
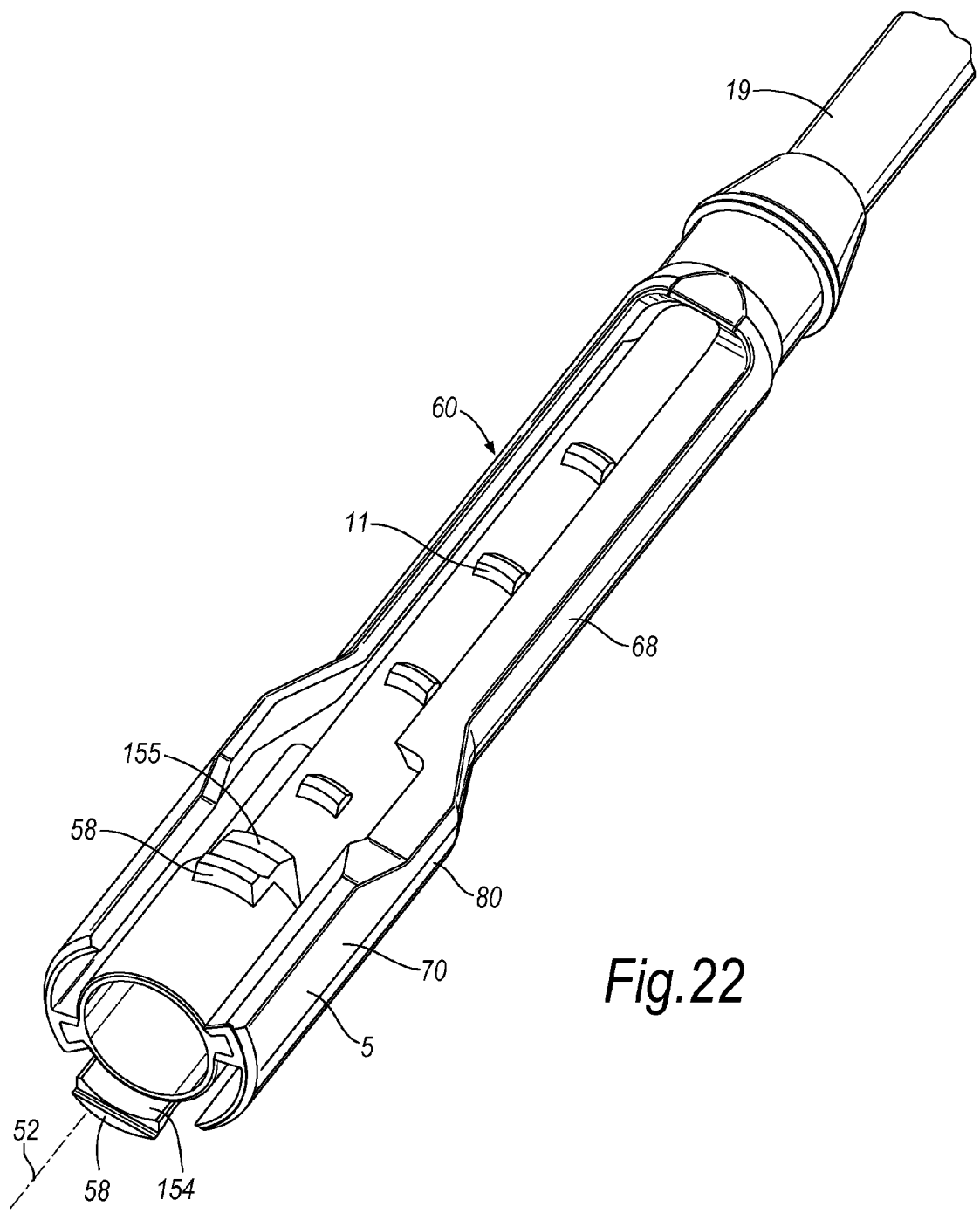
FIG. 22 shows the forward end of the device according to an alternative embodiment of the invention.

Referring to the alternative embodiment shown in FIG. 22, parts which are similar or identical to equivalent parts in the embodiment shown in FIGS. 1 to 21 are given the same reference number. At the forward end of the outer tube 19, there are two fingers 154 and 155 symmetrically circumferentially spaced about the common tube axis 52, one finger 154 extending fully to the forward end of the outer tube 19 while the other finger 155 stops short of that forward end. By providing fingers 154, 155 of different length, a larger pushing surface is available on the shorter finger 155 for pushing a ligating band from the intermediate region 80 up on to the forward region 70 of the sleeve 60. The embodiment of FIG. 22 also differs from that shown in FIGS. 1 to 21 in that a more gentle gradient is provided between the rearward region 68 and the forward region 70 of the sleeve 60. Otherwise the arrangement is similar to that of the embodiment shown in FIGS. 1 to 21.

The invention claimed is:

1. A device for applying successive resilient ligating bands to tissue, said device comprising:
   a) a sleeve having a front end and an opening at said front end, said sleeve having a plurality of axially extending arms having axially extending spaces therebetween, and band-support surfaces located on said arms extending from said front end for accommodating a plurality of ligating bands,
   b) a first tube around which said sleeve is located, said first tube being reciprocal relative to said sleeve in a direction towards and away from the front of said device, said first tube having at least one axially extending finger provided with a plurality of forward-facing pushing surfaces;
   c) means for drawing tissue to be ligated into said opening, d) drive means for driving said first tube relative to said sleeve from a rest position along a first movement path including
   (i) a rotational component to bring said at least one finger from a rest position into alignment with said axially extending spaces between said arms, and
   (ii) a subsequent axial component to advance said first tube towards said front end of said sleeve thereby to cause said pushing surfaces to push said bands forwardly so that they ride along said band-support surfaces of said sleeve to each lie nearer said front end, a foremost band being pushed off said front end of said sleeve onto said tissue; and
e) drive means for returning said first tube to its rest position along a second movement path comprising
   (i) a rotational component to bring said at least one finger behind said arms, and
   (ii) a subsequent axial component to retract said at least one finger into said rest position.

2. The device according to claim 1, wherein said first tube is of circular cross section.

3. The device according to claim 1, wherein said first tube has a plurality of said fingers.

4. The device according to claim 3, wherein said fingers each subtend at said tube axis an angle no greater than that subtended by said arms.

5. The device according to claim 3, wherein said plurality of fingers are symmetrically spaced about said tube axis.

6. The device according to claim 3, wherein said plurality of fingers is equal in number to said plurality of arms.

7. The device according to claim 6, wherein two fingers and two arms are provided.

8. The device as claimed in claim 7, wherein said two fingers are of different length.

9. The device according to claim 1, wherein said sleeve is of circular cross-section and is located concentrically with respect to said first tube.

10. The device according to claim 1, wherein said plurality of arms are symmetrically spaced about said tube axis.

11. The device according to claim 1, wherein said sleeve is connected to a second tube positioned within said first tube, said first tube being capable of sliding and rotational movement relative to said second tube.

12. The device according to claim 1, wherein said pushing surfaces are comprised of a plurality of axially spaced teeth mounted on said at least one finger.

13. The device according to claim 12 wherein additional axially spaced teeth are mounted on said first tube, immediately to said rear of said at least one finger.

14. The device according to claim 1, wherein said drive means for driving said first tube relative to said sleeve along said first movement path includes a cam guide, having a shape defining said first movement path.

15. The device according to claim 1, wherein said drive means for driving said first tube relative to said sleeve along said second movement path includes a cam guide, having a shape defining said second movement path.

16. The device according to claim 1, wherein said drive means for driving said first tube relative to said sleeve includes a manually operable actuator.

17. The device according to claim 1, wherein said sleeve has a region of smaller diameter remote from said front end, at least part of said band-support surfaces being located in said smaller diameter region, said smaller diameter region merging with said larger diameter region by way of a transition portion having a progressively increasing diameter in said direction towards said front end.

18. The device according to claim 1, wherein said arms of said sleeve each have a region of smaller circumference remote from said front end, at least part of said band-support surfaces being located in said smaller circumference region, said smaller circumference region merging with said larger circumference region by way of a transition portion having a progressively increasing circumference in said direction towards said front end.

19. A device as claimed in claim 1, wherein said sleeve is mounted on a second tube positioned within said first tube and wherein said means for drawing tissue into said opening comprises means for establishing a reduced air pressure in said opening via said second tube.

20. A device as claimed in claim 19, adapted such that reduced air pressure is established at said opening as said first tube is driven along said first movement path and is disestablished at said opening in said rest position.

21. A device as claimed in claim 20, wherein said second tube has an aperture in a side wall thereof aligned with an aperture in a side wall of said first tube when said device is in its rest position.

22. A device according to claim 1, together with a plurality of ligating bands mounted on said sleeve and/or on said first tube.

23. A device as claimed in claim 1, wherein said tissue comprises a haemorrhoid.

* * * * *